US006294522B1

(12) United States Patent
Zablocki et al.

(10) Patent No.: US 6,294,522 B1
(45) Date of Patent: Sep. 25, 2001

(54) $N^6$ HETEROCYCLIC 8-MODIFIED ADENOSINE DERIVATIVES

(75) Inventors: Jeff A. Zablocki; Venkata P. Palle, both of Mountain View; Prabha N. Ibrahim, Mountainview; Luiz Belardenelli, Menlo Park, all of CA (US)

(73) Assignee: CV Therapeutics, Inc., Palo Alto, CA (US)

( * ) Notice: Subject to any disclaimer, the term of this patent is extended or adjusted under 35 U.S.C. 154(b) by 0 days.

(21) Appl. No.: 09/454,485

(22) Filed: Dec. 3, 1999

(51) Int. Cl.$^7$ .......................... A61K 31/70; C07H 19/167
(52) U.S. Cl. ...................... 514/46; 536/27.23; 536/27.6; 536/27.61; 536/27.62; 536/27.63
(58) Field of Search ............................... 514/46; 536/27.6, 536/27.61, 27.62, 27.63, 27.23

(56) References Cited

U.S. PATENT DOCUMENTS

| | | | |
|---|---|---|---|
| Re. 35,904 | * | 9/1998 | Paterson et al. .................... 514/24 |
| 2,881,164 | * | 4/1959 | Kissman et al. .................. 536/27.62 |
| 3,150,124 | * | 9/1964 | Svarnas et al. ................... 536/27.62 |
| 4,464,361 | * | 8/1984 | Ohki et al. ............................. 514/46 |
| 4,616,003 | * | 10/1986 | Hamilton et al. ..................... 514/46 |
| 4,755,594 | * | 7/1988 | Bridges et al. ................... 536/27.62 |
| 5,032,583 | * | 7/1991 | Evans .................................... 514/46 |
| 5,055,569 | * | 10/1991 | Becker et al. .................... 536/27.62 |
| 5,432,164 | * | 7/1995 | Knutsen et al. ....................... 514/46 |
| 5,683,989 | * | 11/1997 | Lau et al. .............................. 514/46 |
| 5,789,419 | | 8/1998 | Lum et al. . |
| 5,843,916 | * | 12/1998 | Cho-Chung et al. ................ 514/47 |

FOREIGN PATENT DOCUMENTS

07324035 * 12/1995 (JP) .

OTHER PUBLICATIONS

B. Lerman et al, "Cardiac Electrophysiology of Adenosine", Circulation, vol. 83 (1991) p. 1499–1509 (Issue No. 5; May 1991).
J.C. Shryock, "Adenosine and Adenosine Receptors in the Cardiovascular System: Biochemistry, Physiology, and Pharmacology", The Am. J. Cardiology, vol. 79 (1997) p. 2–10 (Issue No. 12A; Jun. 19, 1997).
J.D. Thornton, "Intravenous Pretreatment with $A_1$–Selective Adenosine Analogues Protects the Heart Aginst Infarction". Circulation, vol. 85 (1992), p. 659–665 (Feb. 1992).
E. A. van Schaick et al., J., "Physiological Indirect Effect Modeling of the Antilipolytic Effects of Adenosine $A_1$–Receptor Agonists", Pharmacokinetics and Biopharmaceutics, vol. 25 (1997) p. 673–694. Month of publication data is unavailable for this reference.
P. Strong, " Suppression of non–esterified fatty acids and triacylglycerol in experimental animals by the adenosine analogue GR79236", Clinical Science, vol. 84 (1993), p. 663–669. Month of publication data is unavailable for this reference.

D. Thiebaud et al, "Effect of Long Chain Triglyceride Infusion on Glucose Metabolism in Man", Metab. Clin. Exp., vol. 31 (1982), p. 1128–1136 (Issue No. 11; Nov., 1982.
G. Boden et al., "Mechanism of Fatty–Acid–Induced Inhibition of Glucose Uptake", J. Clin. Invest., vol. 93, (1994) p. 2438–2446 (Jun., 1994).
P.J. Randle et al., "The Glucose Fatty–Acid Cycle Its Role in Insulin Sensitivity and the Metabolic Disturbances of Diabetes Mellitus", Lancet (1963) p. 785–789 (Apr. 13, 1963).
Klitgaard, et al., "Contrasting Effects of Adenosine $A_1$ and $A_2$ Receptor Ligands in Different Chemoconvulsive Rodent Models," Eur. J. Pharmacol (1993), vol. 224, pp. 221–228. Month of publication data is unavailable for this reference.
G. Zhang, "Activation of adenosine A1 receptors underlies anticonvulsant effect of CGS21680", Eur. J. Pharmacol, vol. 255 (1994), p. 239–243. Month of publication data is unavailable for this reference.
Knutsen, "N–Substituted Adenosines as Novel Neuroprotective A1 Agonists with Diminished Hypotensive Effects", J. Med. Chem., vol. 42 (1999) p. 3463–3477. Month of publication data is unavailable for this reference.
Vergauwen, et al., "Adenosine Receptors Mediate Synergistic Stimulation of Glucose Uptake and Transport by Insulin and by Contractions in Rat Skeletal Muscle", J. Clin. Invest, (1994) 93, 974–81 (Mar., 1994).
Gellai, et al., "CVT–124, a Novel Adenosine A1 Receptor Antagonist with Unique Diuretic Activity", JPET, (1998) 286, p. 1191–6. Month of publication data is unavailable for this reference.
Wilcox. et al., "Natriuretic and Diuretic Actions of a Highly Selective Adenosine $A_1$ Receptor Anagonist," J. Am. Soc. Nephrol, (1999) 10, p. 714–720. Month of publication data is unavailable for this reference.
R.B. Clark, et al., "Partial agonists and G protein–coupled receptor desensitization", TiPS, vol. 20 (1999), p. 279–286 (Jul., 1999).
D. M. Dennis et al., "Homologous Desensitization of the A1–Adenosine Receptor System in the Guinea Pig Atrioventricular Node," JPET, vol. 272 (1995), p. 1024–1035. Month of publication data is unavailable for this reference.
Parsons, J., "Heterologous Desensitization of the Inhbitory A1 Adenosine Receptor–Adenylate Cyclase System in Rat Adipocytes", Biol. Chem. vol. 262 (Jan. 1987) p. 841–847.

* cited by examiner

Primary Examiner—Gary Geist
Assistant Examiner—L. Eric Crane
(74) Attorney, Agent, or Firm—McDonnell Boehnen Hulbert & Berghoff

(57) ABSTRACT

$N^6$ heterocyclic 8 modified adenosine derivatives that are selective, partial or full adenosine $A_1$ receptor partial or full agonists, and as such, are useful for modifying cardiac activity, modifying adipocyte function, treating central nervous system disorders, and treating diabetic disorders and obesity in mammals, and especially in humans.

24 Claims, No Drawings

$N^6$ HETEROCYCLIC 8-MODIFIED ADENOSINE DERIVATIVES

BACKGROUND OF THE INVENTION

(1) Field of the Invention

There is provided useful drugs and pro-drugs that are $N^6$ heterocyclic 8 modified adenosine derivatives. The compositions of this invention are selective, partial or full adenosine $A_1$ receptor agonists, and as such, are useful for modifying cardiac activity, modifying adipocyte function, treating central nervous system disorders, and treating diabetic disorders and obesity in mammals, and especially in humans.

(2) Description of the Art

There are at least two subtypes of adenosine receptors in the heart: $A_1$ and $A_{2A}$. Each subtype affects different physiological functions. The $A_1$ adenosine receptor mediates two distinct physiological responses. Inhibition of the cardiostimulatory effects of catecholamine are mediated via the inhibition of adenylate cyclase, whereas the direct effects to slow the heart rate (HR) and to prolong impulse propagation through the AV node are due in great part to activation of $I_{KAdo}$. (B. Lerman and L. Belardinelli Circulation, Vol. 83 (1991), P 1499–1509 and J. C. Shryock and L. Belardinelli The Am. J. Cardiology, Vol. 79 (1997) P 2–10). Both, the anti-β-adrenergic action and direct depressant effects on SA and AV nodal function are mediated by the $A_1$ receptor; there is no role for the $A_{2A}$ receptor in this response to adenosine. $A_{2A}$ receptors mediate the coronary vasodilatation caused by adenosine. Stimulation of the $A_1$ adenosine receptor accordingly shortens the duration and decreases the amplitude of the action potential of AV nodal cells, and hence prolongs the refractory period of the AV nodal cell. The consequence of these effects is to limit the number of impulses conducted from the atria to the ventricles. This forms the basis of the clinical utility of $A_1$ receptor agonists for the treatment of supraventricular tachycardias, including termination of nodal re-entrant tachycardias, and control of ventricular rate during atrial fibrillation and flutter.

A clinical utility of $A_1$ agonists therefore is in the treatment of acute and chronic disorders of heart rhythm, especially those diseases characterized by rapid heart rate where the rate is driven by abnormalities in the sinoatrial, atria, and AV nodal tissues. Such disorders include but are not limited to atrial fibrillation, supraventricular tachycardia and atrial flutter. Exposure to $A_1$ agonists causes a reduction in the heart rate and a regularization of the abnormal rhythm thereby improving cardiovascular function.

$A_1$ agonists, through their ability to inhibit the effects of catecholamines, decrease cellular cAMP, and thus, should have beneficial effects in the failing heart where increased sympathetic tone increases cellular cAMP levels. The latter has been shown to be associated with increased likelihood of ventricular arrhythmias and sudden death. $A_1$ 1 of the above concepts are discussed in reviews regarding the effects of adenosine on cardiac electrophysiology (see B. Lerman and L. Belardinelli Circulation, Vol. 83 (1991), P 1499–1509 and J. C. Shryock and L. Belardinelli, Am. J. Cardiology, Vol. 79 (1997) P 2–10).

A controversial area in the field of $A_1$ adenosine agonism is that the benefit of preconditioning of the heart prior to ischemia may be due to binding of adenosine to the $A_1$ receptor. Evidence for this hypothesis comes from a rabbit ischemia model wherein 2-chloro-N6-cyclopentyladenosine (CCPA) and R-PIA were administered prior to ischemia providing protection with respect to infarct size (J. D. Thornton et al. Circulation Vol. 85 (1992) 659–665).

$A_1$ agonists, as a result of their inhibitory action on cyclic AMP generation, have antilipolytic effects in adipocytes that leads to a decreased release of nonesterified fatty acids (NEFA) (E. A. van Schaick et al J. Pharmacokinetics and Biopharmaceutics, Vol. 25 (1997) p 673–694 and P. Strong Clinical Science Vol. 84 (1993) p. 663–669). Non-insulin-dependent diabetes mellitus (NIDDM) is characterized by an insulin resistance that results in hyperglycemia. Factors contributing to the observed hyperglycemia are a lack of normal glucose uptake and activation of skeletal muscle glycogen synthase (GS). Elevated levels of NEFA have been shown to inhibit insulin-stimulated glucose uptake and glycogen synthesis ( D. Thiebaud et al Metab. Clin. Exp. Vol. 31 (1982) p 1128–1136 and G. Boden et al J. Clin. Invest. Vol. 93 (1994) p 2438–2446). The hypothesis of a glucose fatty acid cycle was proposed by P. J. Randle as early as 1963 (P. J. Randle et al Lancet (1963) p. 785–789). A tenet of this hypothesis would be that limiting the supply of fatty acids to the peripheral tissues should promote carbohydrate utilization (P. Strong et al Clinical Science Vol. 84 (1993) p. 663–669).

The benefit of an $A_1$ agonist in central nervous disorders has been reviewed and the content are included herein by reference (L. J. S. Knutsen and T. F. Murray In Purinergic Approaches in Experimental Therapeutics, Eds. K. A. Jacobson and M. F. Jarvis (1997) Wiley-Liss, N.Y., P -423–470). Briefly, based on experimental models of epilepsy, a mixed $A_{2A}$: $A_1$ agonist, metrifudil, has been shown to be a potent anticonvulsant against seizures induced by the inverse benzodiazepine agonist methyl 6,7-dimethoxy-4-ethyl-beta-carboline-3-carboxylate (DMCM, H. Klitgaard Eur. J. Pharmacol. (1993) Vol. 224 p. 221–228). In other studies using CGS 21680, an $A_{2A}$ agonist, it was concluded that the anticonvulsant activity was attributed to activation of the $A_1$ receptor (G. Zhang et al. Eur. J. Pharmacol. Vol. 255 (1994) p. 239–243). Furthermore, $A_1$ adenosine selective agonists have been shown to have anticonvulsant activity in the DMCM model (L. J. S. Knutsen In Adenosine and Adenne Nucleotides: From Molecular Biology to Integrative Physiology; eds. L. Belardinelli and A. Pelleg, Kluwer: Boston, 1995, pp 479–487). A second area where an $A_1$ adenosine agonist has a benefit is in animal models of forebrain ishemia as demonstrated by Knutsen et al (J. Med. Chem. Vol. 42 (1999) p. 3463–3477). The benefit in neuroprotection is believed to be in part due to the inhibition of the release of excitatory amino acids (ibid).

There are a number of full $A_1$ agonists disclosed in the prior art. However, the agonists disclosed are generally in the forms that are not useful in the mammalian body. Because useful forms of $A_1$ agonists may not always be stable, soluble or they may have other properties that make their incorporation into therapeutic dosage forms difficult, it is often necessary to identify compositions that are more easily incorporated into therapeutic dosage forms in order to provide the desired therapeutic effect. $A_1$ so, these agonists fail as useful therapeutics due to side effects caused by the non-selective stimulation of the $A_1$ adenosine receptor in all biologically available tissues and the desensitization of the desired response preempting their use as chronic agents. Therefore, there remains a need for specific and selective $A_1$ agonists, precursors and/or pro-drugs that are converted in the body into useful therapeutic compositions.

SUMMARY OF THE INVENTION

This invention includes heterocyclic 8 modified adenosine derivative compositions that are useful partial or full adenosine $A_1$ receptor agonists.

This invention also includes pharmaceutical compositions including one or more heterocyclic 8 modified adenosine derivative compositions.

In still another embodiment, this invention includes heterocyclic 8 modified adenosine derivatives having the formula:

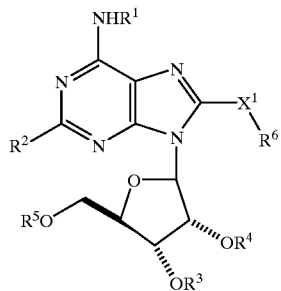

In yet another embodiment, this invention includes methods for administering compositions of this invention to mammals, and especially to humans, to stimulate coronary activity, to modify adipocyte function, to treat central nervous system disorders, and to treat diabetic disorders.

In a further embodiment, this invention is pharmaceutical compositions of matter comprising at least one composition of this invention and one or more pharmaceutical excipients.

DESCRIPTION OF THE CURRENT EMBODIMENT

This invention includes a class of heterocyclic 8 modified adenosine derivatives having the formula:

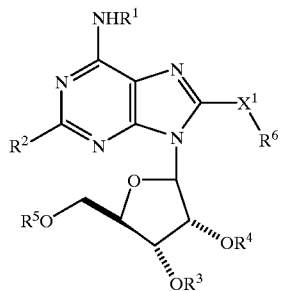

wherein $X^1$=O, S, $NR^7$;

$R^1$ is a monocyclic or polycyclic heterocyclic group containing from 3 to 15 carbon atoms wherein at least one carbon atom is replaced with an atom or molecule selected from the group consisting of N, O, P and S—(O)$_{0-2}$ and wherein $R^1$ does not contain an epoxide group;

Wherein $R^2$ is selected from the group consisting of hydrogen, halo, $CF_3$, and cyano;

Wherein $R^3$, $R^4$, and $R^5$ are independently selected from the group consisting of hydrogen, —(CO)—R', —(CO)—R", and —(CO)—R''' wherein R', R", and R''' are independently selected from the group consisting of $C_{1-15}$ alkyl, $C_{2-15}$ alkenyl, $C_{2-15}$ alkynyl, heterocyclyl, aryl, and heteroaryl, which alkyl, alkenyl, alkynyl, aryl, heterocyclyl, and heteroaryl are optionally substituted with 1 to 3 substituents independently selected from the group of halo, $NO_2$, alkyl, heterocyclyl, aryl, heteroaryl, $CF_3$, CN, $OR^{20}$, $SR^{20}$, $S(O)R^{22}$, $SO_2R^{22}$, $SO_2N(R^{20})_2$, $SO_2NR^{20}COR^{22}$, $SO_2NR^{22}CO_2R^{22}$, $SO_2NR^{20}CON(R^{20})_2$, $NR^{20}COR^{22}$, $NR^{20}CO_2R^{22}$, $NR^{20}CON(R^{20})_2$, $NR^{20}C(NR^{20})NHR^{23}$, $COR^{20}$, $CO_2R^{20}$, $CON(R^{20})_2$, $CONR^{20}SO_2R^{22}$, $NR^{20}SO_2R^{22}$, $SO_2NR^{20}CO_2R^{22}$, $OCONR^{20}SO_2R^{22}$, OC(O)$R^{20}$, $C(O)OCH_2OC(O)R^{20}$, and $OCON(R^{20})_2$ and wherein each optional heteroaryl, aryl, alkyl, and heterocyclyl substituent is optionally further substituted with halo, $NO_2$, alkyl, $CF_3$, amino, mono- or di- alkylamino, alkyl or aryl or heteroaryl amide, $NR^{20}COR^{22}$, $NR^{20}SO_2R^{22}$, $COR^{20}$, $CO_2R^{20}$, $CON(R^{20})_2$, $NR^{20}CON(R^{20})_2$, $OC(O)R^{20}$, $OC(O)N(R^{20})_2$, $SR^{20}$, $S(O)R^{22}$, $SO_2R^{22}$, $SO_2N(R^{20})_2$, CN, or $OR^{20}$;

$R^6$ and $R^7$ are independently selected from the group consisting of hydrogen, $C_{1-15}$ alkyl, $C_{2-15}$ alkenyl, $C_{2-15}$ alkynyl, heterocyclyl, aryl, and heteroaryl, wherein the alkyl, alkenyl, alkynyl, aryl, heterocyclyl and heteroaryl substituents are optionally substituted with from 1 to 3 substituents independently selected from the group consisting of halo, alkyl, $NO_2$, heterocyclyl, aryl, heteroaryl, $CF_3$, CN, $OR^{20}$, $SR^{20}$, $N(R^{20})_2$, $S(O)R^{22}$, $SO_2R^{22}$, $SO_2N(R^{20})_2$, $SO_2NR^{20}COR^{22}$, $SO_2NR^{20}CO_2R^{22}$, $S(O)_3R^{20}$, $P(O)(OR^{20})_2$, $SO_2NR^{20}CON(R^{20})_2$, $NR^{20}COR^{22}$, $NR^{20}CO_2R^{22}$, $NR^{20}CON(R^{20})_2$, $NR^{20}C(NR^{20})NHR^{23}$, $COR^{20}$, $CO_2R^{20}$, $CON(R^{20})_2$, $CONR^{20}SO_2R^{22}$, $NR^{20}SO_2R^{22}$, $SO_2NR^{20}CO_2R^{22}$, $OCONR^{20}SO_2R^{22}$, $OC(O)R^{20}$, $C(O)OCH_2OC(O)R^{20}$, and $OCON(R^{20})_2$ and wherein each optional heteroaryl, aryl, and heterocyclyl substituent is optionally further substituted with halo, $NO_2$, alkyl, $CF_3$, amino, mono- or di- alkylamino, alkyl or aryl or heteroaryl amide, $NR^{20}COR^{22}$, $NR^{20}SO_2R^{22}$, $COR^{20}$, $CO_2R^{20}$, $CON(R^{20})_2$, $NR^{20}CON(R^{20})_2$, $OC(O)R^{20}$, $OC(O)N(R^{20})_2$, $SR^{20}$, $S(O)_3R^{20}$, $P(O)(OR^{20})_2$, $S(O)R^{22}$, $SO_2R^{22}$, $SO_2N(R^{20})_2$, CN, or $OR^{20}$;

$R^{20}$ is selected from the group consisting of H, $C_{1-15}$ alkyl, $C_{2-15}$ alkenyl, $C_{2-15}$ alkynyl, heterocyclyl, aryl, and heteroaryl, wherein the alkyl, alkenyl, alkynyl, heterocyclyl, aryl, and heteroaryl substituents are optionally substituted with from 1 to 3 substituents independently selected from halo, alkyl, mono- or dialkylamino, alkyl or aryl or heteroaryl amide, CN, O—$C_{1-6}$ alkyl, $CF_3$, aryl, and heteroaryl; and $R^{22}$ is selected from the group consisting of $C_{1-15}$ alkyl, $C_{2-15}$ alkenyl, $C_{2-15}$ alkynyl, heterocyclyl, aryl, and heteroaryl, wherein the alkyl, alkenyl, alkynyl, heterocyclyl, aryl, and heteroaryl substituents are optionally substituted with from 1 to 3 substituents independently selected from halo, alkyl, mono- or dialkylamino, alkyl or aryl or heteroaryl amide, CN, O—$C_{1-6}$ alkyl, $CF_3$, aryl, and heteroaryl.

In more preferred compositions, $X^1$=$NR^7$; $R^2$ is hydrogen; $R^3$, $R^4$, and $R^5$ are each independently selected from the group consisting of hydrogen, —(CO)—R', —(CO)—R", or —(CO)—R''' wherein R', R", and R''' are independently selected from the group consisting of $C_{1-6}$ alkyl, and preferably methyl; $R^6$ is selected from the group consisting of $C_{1-3}$ alkyl and hydrogen with hydrogen being preferred; $R^7$ is independently selected from the group consisting of hydrogen, $C_{1-6}$ alkyl, $C_{2-6}$ alkenyl, and $C_{2-6}$ alkynyl, wherein the alkyl, alkenyl, and alkynyl substituents are optionally substituted with 1 substituent independently selected from the group consisting of alkyl, aryl, $CF_3$, $OR^{20}$, $SR^{20}$, $CO_2R^{20}$, $S(O)_3R^{20}$, and wherein optional aryl substituent is optionally further substituted with halo, alkyl, $CF_3$; and $R^{20}$ is selected from the group consisting of H, $C_{1-6}$ alkyl.

In another preferred group of compositions, $X^1$=$NR^7$; $R^2$ is hydrogen; $R^3$, $R^4$, $R^5$ and $R^6$ are each hydrogen; and $R^7$ is $C_{1-6}$ alkyl wherein the alkyl, is optionally substituted with 1 substituent selected from the group consisting of alkyl or aryl wherein the optional aryl substituent is further optionally substituted with halo, alkyl, and CF$_3$. More preferably, R$^7$ is C$_{1-4}$ alkyl that is optionally substituted with phenyl.

In another preferred class of compositions, X$^1$=NR$^7$; R$^2$, R$^3$, R$^4$, R$^5$, and R$^6$ are each hydrogen; and R$^7$ is C$_{2-4}$ alkenyl that is optionally substituted with 1 substituent selected from the group consisting of alkyl and aryl. More preferably, R$^7$ is C$_{2-3}$ alkenyl.

In yet another preferred class of compositions, X$^1$=NR$^7$; R$^2$, R$^3$, R$^4$, R$^5$, and R$^6$ are each hydrogen; and R$^7$ is C$_{2-4}$ alkynyl that is optionally substituted with 1 substituent selected from the group consisting of alkyl or aryl. More preferably, R$^7$ is C$_{2-3}$ alkynyl.

In the compositions of this invention, R$^1$ is preferably mono or polysubstituted with one or more compounds selected from the group consisting of halogen, oxo, hydroxyl, lower alkyl, substituted lower alkyl, alkoxy, aryl, acyl, aryloxy, carboxyl, substituted aryl, heterocycle, heteroaryl, substituted heteroaryl, cycloalkyl, substituted cycloalkyl, nitro, cyano and mixtures thereof. More preferably, R$^1$ is a monocyclic, bicyclic, or tricyclic cycloalkyl group containing from 3 to 15 carbon atoms wherein at least one carbon atom is substituted with an atom or molecule selected from the group consisting of O or S—(O)$_{0-2}$.

One example of a preferred R$^1$ moiety is:

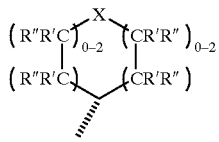

Wherein X is O, or S (—O)$_{0-2}$; and R' and R" are individually selected from the group consisting of hydrogen, halogen, hydroxyl, lower alkyl, substituted lower alkyl, alkoxy, aryl, acyl, aryloxy, carboxyl, substituted aryl, heterocycle, heteroaryl, substituted heteroaryl, cycloalkyl, substituted cycloalkyl, nitro, and cyano, and alternatively, any CR'R" may be C=O.

Most preferably, R$^1$ is selected from the group consisting of 3-tetrahydrofuranyl, 3-tetrahydrothiofuranyl, 4-pyranyl, and 4 thiopyranyl.

Most preferred compositions of this invention are selected from the group consisting of N$^6$-{3-(3R)tetrahydrofuranyl}-8-isopropylaminoadenosine, N$^6$-{3-(3R)tetrahydroftiranyl}-8-(2-propyl)aminoadenosine, N$^6$-{3-(3R)tetrahydrofuranyl}-8-allylaminoadenosine, N$^6$-{3-(3R)tetrahydrofuranyl}-8-(2-propenyl)aminoadenosine, N$^6$-{3-(3R)tetrahydrofuranyl}-8-ethylarninoadenosine, N$^6$-{3-(3R)tetrahydrofuranyl}-8-propylaminoadenosine, N$^6$-{3-(3R)tetrahydrofuranyl}-8-butylaminoadenosine, N$^6$-{3-(3R)tetrahydrofuranyl}-8-benzylaminoadenosine, N$^6$-{3-(3R)tetrahydrofuranyl}-8-methylaminoadenosine, and N$^6$-{3-(3R)tetrahydrofuranyl}-8-isopropylamino-2',3',5'-tri-O-acetyladenosine.

The following definitions apply to terms as used herein.

"Halo" or "Halogen"—alone or in combination means all halogens, that is, chloro (Cl), fluoro (F), bromo (Br), iodo (I).

"Hydroxyl" refers to the group —OH.

"Thiol" or "mercapto" refers to the group —SH.

"Alkyl"—alone or in combination means an alkane-derived radical containing from 1 to 20, preferably 1 to 15, carbon atoms (unless specifically defined). It is a straight chain alkyl, branched alkyl or cycloalkyl. Preferably, straight or branched alkyl groups containing from 1–15, more preferably 1 to 8, even more preferably 1–6, yet more preferably 1–4 and most preferably 1–2, carbon atoms, such as methyl, ethyl, propyl, isopropyl, butyl, t-butyl and the like. The term "lower alkyl" is used herein to describe the straight chain alkyl groups described immediately above. Preferably, cycloalkyl groups are monocyclic, bicyclic or tricyclic ring systems of 3–8, more preferably 3–6, ring members per ring, such as cyclopropyl, cyclopentyl, cyclohexyl, adamantyl and the like. Alkyl also includes a straight chain or branched alkyl group that contains or is interrupted by a cycloalkyl portion. The straight chain or branched alkyl group is attached at any available point to produce a stable compound. Examples of this include, but are not limited to, 4-(isopropyl)-cyclohexylethyl or 2-methyl-cyclopropylpentyl. A substituted alkyl is a straight chain alkyl, branched alkyl, or cycloalkyl group defined previously, independently substituted with 1 to 3 groups or substituents of halo, hydroxy, alkoxy, alkylthio, alkylsulfinyl, alkylsulfonyl, acyloxy, aryloxy, heteroaryloxy, amino optionally mono- or di-substituted with alkyl, aryl or heteroaryl groups, amidino, urea optionally substituted with alkyl, aryl, heteroaryl or heterocyclyl groups, aminosulfonyl optionally N-mono- or N,N-di-substituted with alkyl, aryl or heteroaryl groups, alkylsulfonylamino, arylsulfonylamino, heteroarylsulfonylamino, alkylcarbonylamino, arylcarbonylamino, heteroarylcarbonylamino, or the like.

"Alkenyl"—alone or in combination means a straight, branched, or cyclic hydrocarbon containing 2–20, preferably 2–17, more preferably 2–10, even more preferably 2–8, most preferably 2–4, carbon atoms and at least one, preferably 1–3, more preferably 1–2, most preferably one, carbon to carbon double bond. In the case of a cycloalkyl group, conjugation of more than one carbon to carbon double bond is not such as to confer aromaticity to the ring. Carbon to carbon double bonds may be either contained within a cycloalkyl portion, with the exception of cyclopropyl, or within a straight chain or branched portion. Examples of alkenyl groups include ethenyl, propenyl, isopropenyl, butenyl, cyclohexenyl, cyclohexenylalkyl and the like. A substituted alkenyl is the straight chain alkenyl, branched alkenyl or cycloalkenyl group defined previously, independently substituted with 1 to 3 groups or substituents of halo, hydroxy, alkoxy, alkylthio, alkylsulfinyl, alkylsulfonyl, acyloxy, aryloxy, heteroaryloxy, amino optionally mono- or di-substituted with alkyl, aryl or heteroaryl groups, amidino, urea optionally substituted with alkyl, aryl, heteroaryl or heterocyclyl groups, aminosulfonyl optionally N-mono- or N,N-di-substituted with alkyl, aryl or heteroaryl groups, alkylsulfonylamino, arylsulfonylamino, heteroarylsulfonylamino, alkylcarbonylamino, arylcarbonylamino, heteroarylcarbonylamino, carboxy, alkoxycarbonyl, aryloxycarbonyl, heteroaryloxycarbonyl, or the like attached at any available point to produce a stable compound.

"Alkynyl"—alone or in combination means a straight or branched hydrocarbon containing 2–20, preferably 2–17, more preferably 2–10, even more preferably 2–8, most preferably 2–4, carbon atoms containing at least one, preferably one, carbon to carbon triple bond. Examples of alkynyl groups include ethynyl, propynyl, butynyl and the like. A substituted alkynyl refers to the straight chain alkynyl or branched alkenyl defined previously, independently substituted with 1 to 3 groups or substituents of halo, hydroxy, alkoxy, alkylthio, alkylsulfinyl, alkylsulfonyl, acyloxy, aryloxy, heteroaryloxy, amino optionally mono- or di-substituted with alkyl, aryl or heteroaryl groups, amidino, urea optionally substituted with alkyl, aryl, heteroaryl or heterocyclyl groups, aminosulfonyl optionally N-mono- or N,N-di-substituted with alkyl, aryl or heteroaryl groups, alkylsulfonylamino, arylsulfonylamino, heteroarylsulfonylamino, alkylcarbonylamino, arylcarbonylamino, heteroarylcarbonylamino, or the like attached at any available point to produce a stable compound.

"Alkyl alkenyl" refers to a group —R—CR'=CR''' R''', where R is lower alkyl, or substituted lower alkyl, R', R''', R''' may independently be hydrogen, halogen, lower alkyl, substituted lower alkyl, acyl, aryl, substituted aryl, hetaryl, or substituted hetaryl as defined below.

"Alkyl alkynyl" refers to a groups —RC≡CR' where R is lower alkyl or substituted lower alkyl, R' is hydrogen, lower alkyl, substituted lower alkyl, acyl, aryl, substituted aryl, hetaryl, or substituted hetaryl as defined below.

"Alkoxy" denotes the group —OR, where R is lower alkyl, substituted lower alkyl, acyl, aryl, substituted aryl, aralkyl, substituted aralkyl, heteroalkyl, heteroarylalkyl, cycloalkyl, substituted cycloalkyl, cycloheteroalkyl, or substituted cycloheteroalkyl as defined.

"Alkylthio" denotes the group —SR, —S(O)$_{n=1-2}$—R, where R is lower alkyl, substituted lower alkyl, aryl, substituted aryl, aralkyl or substituted aralkyl as defined herein.

"Acyl" denotes groups —C(O)R, where R is hydrogen, lower alkyl substituted lower alkyl, aryl, substituted aryl and the like as defined herein.

"Aryloxy" denotes groups —OAr, where Ar is an aryl, substituted aryl, heteroaryl, or substituted heteroaryl group as defined herein.

"Amino" denotes the group NRR', where R and R' may independently by hydrogen, lower alkyl, substituted lower alkyl, aryl, substituted aryl, hetaryl, or substituted hetaryl as defined herein or acyl.

"Amido" denotes the group —C(O)NRR', where R and R' may independently by hydrogen, lower alkyl, substituted lower alkyl, aryl, substituted aryl, hetaryl, substituted hetaryl as defined herein.

"Carboxyl" denotes the group —C(O)OR, where R is hydrogen, lower alkyl, substituted lower alkyl, aryl, substituted aryl, hetaryl, and substituted hetaryl as defined herein.

"Aryl"—alone or in combination means phenyl or naphthyl optionally carbocyclic fused with a cycloalkyl of preferably 5–7, more preferably 5–6, ring members and/or optionally substituted with 1 to 3 groups or substituents of halo, hydroxy, alkoxy, alkylthio, alkylsulfinyl, alkylsulfonyl, acyloxy, aryloxy, heteroaryloxy, amino optionally mono- or di-substituted with alkyl, aryl or heteroaryl groups, amidino, urea optionally substituted with alkyl, aryl, heteroaryl or heterocyclyl groups, aminosulfonyl optionally N-mono- or N,N-di-substituted with alkyl, aryl or heteroaryl groups, alkylsulfonylamino, arylsulfonylamino, heteroarylsulfonylamino, alkylcarbonylamino, arylcarbonylamino, heteroarylcarbonylamino, or the like.

"Substituted aryl" refers to aryl optionally substituted with one or more functional groups, e.g., halogen, lower alkyl, lower alkoxy, alkylthio, acetylene, amino, amido, carboxyl, hydroxyl, aryl, aryloxy, heterocycle, hetaryl, substituted hetaryl, nitro, cyano, thiol, sulfamido and the like.

"Heterocycle" refers to a saturated, unsaturated, or aromatic carbocyclic group having a single ring (e.g., morpholino, pyridyl or furyl) or multiple condensed rings (e.g., naphthpyridyl, quinoxalyl, quinolinyl, indolizinyl or benzo[b]thienyl) and having at least one hetero atom, such as N, O or S, within the ring, which can optionally be unsubstituted or substituted with, e.g., halogen, lower alkyl, lower alkoxy, alkylthio, acetylene, amino, amido, carboxyl, hydroxyl, aryl, aryloxy, heterocycle, hetaryl, substituted hetaryl, nitro, cyano, thiol, sulfamido and the like.

"Heteroaryl"—alone or in combination means a monocyclic aromatic ring structure containing 5 or 6 ring atoms, or a bicyclic aromatic group having 8 to 10 atoms, containing one or more, preferably 1–4, more preferably 1–3, even more preferably 1–2, heteroatoms independently selected from the group O, S, and N, and optionally substituted with 1 to 3 groups or substituents of halo, hydroxy, alkoxy, alkylthio, alkylsulfinyl, alkylsulfonyl, acyloxy, aryloxy, heteroaryloxy, amino optionally mono- or di-substituted with alkyl, aryl or heteroaryl groups, amidino, urea optionally substituted with alkyl, aryl, heteroaryl or heterocyclyl groups, aminosulfonyl optionally N-mono- or N,N-di-substituted with alkyl, aryl or heteroaryl groups, alkylsulfonylamino, arylsulfonylamino, heteroarylsulfonylamino, alkylcarbonylamino, arylcarbonylamino, heteroarylcarbonylamino, or the like. Heteroaryl is also intended to include oxidized S or N, such as sulfinyl, sulfonyl and N-oxide of a tertiary ring nitrogen. A carbon or nitrogen atom is the point of attachment of the heteroaryl ring structure such that a stable aromatic ring is retained. Examples of heteroaryl groups are pyridinyl, pyridazinyl, pyrazinyl, quinazolinyl, purinyl, indolyl, quinolinyl, pyrimidinyl, pyrrolyl, oxazolyl, thiazolyl, thienyl, isoxazolyl, oxathiadiazolyl, isothiazolyl, tetrazolyl, imidazolyl, triazinyl, furanyl, benzofuryl, indolyl and the like. A substituted heteroaryl contains a substituent attached at an available carbon or nitrogen to produce a stable compound.

"Heterocyclyl"—alone or in combination means a non-aromatic cycloalkyl group having from 5 to 10 atoms in which from 1 to 3 carbon atoms in the ring are replaced by heteroatoms of O, S or N, and are optionally benzo fused or fused heteroaryl of 5–6 ring members and/or are optionally substituted as in the case of cycloalkyl. Heterocycyl is also intended to include oxidized S or N, such as sulfinyl, sulfonyl and N-oxide of a tertiary ring nitrogen. The point of attachment is at a carbon or nitrogen atom. Examples of heterocyclyl groups are tetrahydrofuranyl, dihydropyridinyl, piperidinyl, pyrrolidinyl, piperazinyl, dihydrobenzofuryl, dihydroindolyl, and the like. A substituted hetercyclyl contains a substituent nitrogen attached at an available carbon or nitrogen to produce a stable compound.

"Substituted heteroaryl" refers to a heterocycle optionally mono or poly substituted with one or more functional groups, e.g., halogen, lower alkyl, lower alkoxy, alkylthio, acetylene, amino, amido, carboxyl, hydroxyl, aryl, aryloxy, heterocycle, substituted heterocycle, hetaryl, substituted hetaryl, nitro, cyano, thiol, sulfamido and the like.

"Aralkyl" refers to the group —R—Ar where Ar is an aryl group and R is lower alkyl or substituted lower alkyl group. Aryl groups can optionally be unsubstituted or substituted with, e.g., halogen, lower alkyl, alkoxy, alkylthio, acetylene, amino, amido, carboxyl, hydroxyl, aryl, aryloxy, heterocycle, substituted heterocycle, hetaryl, substituted hetaryl, nitro, cyano, thiol, sulfamido and the like.

"Heteroalkyl" refers to the group —R—Het where Het is a heterocycle group and R is a lower alkyl group. Heteroalkyl groups can optionally be unsubstituted or substituted with e.g., halogen, lower alkyl, lower alkoxy, alkylthio, acetylene, amino, amido, carboxyl, aryl, aryloxy, heterocycle, substituted heterocycle, hetaryl, substituted hetaryl, nitro, cyano, thiol, sulfamido and the like.

"Heteroarylalkyl" refers to the group —R—HetAr where HetAr is an heteroaryl group and R lower alkyl or substituted lower alkyl. Heteroarylalkyl groups can optionally be unsubstituted or substituted with, e.g., halogen, lower alkyl, substituted lower alkyl, alkoxy, alkylthio, acetylene, aryl, aryloxy, heterocycle, substituted heterocycle, hetaryl, substituted hetaryl, nitro, cyano, thiol, sulfamido and the like.

"Cycloalkyl" refers to a divalent cyclic or polycyclic alkyl group containing 3 to 15 carbon atoms.

"Substituted cycloalkyl" refers to a cycloalkyl group comprising one or more substituents with, e.g., halogen, lower alkyl, substituted lower alkyl, alkoxy, alkylthio, acetylene, aryl, aryloxy, heterocycle, substituted heterocycle, hetaryl, substituted hetaryl, nitro, cyano, thiol, sulfamido and the like.

"Cycloheteroalkyl" refers to a cycloalkyl group wherein one or more of the ring carbon atoms is replaced with a heteroatom (e.g., N, O, S or P).

"Substituted cycloheteroalkyl" refers to a cycloheteroalkyl group as herein defined which contains one or more substituents, such as halogen, lower alkyl, lower alkoxy, alkylthio, acetylene, amino, amido, carboxyl, hydroxyl, aryl, aryloxy, heterocycle, substituted heterocycle, hetaryl, substituted hetaryl, nitro, cyano, thiol, sulfamido and the like.

hydroxyl, aryl, aryloxy, heterocycle, substituted heterocycle, hetaryl, substituted hetaryl, nitro, cyano, thiol, sulfamido and the like.

The compounds of this invention can be prepared as outlined in Schemes 1–4, below. Compounds having the general formula IV can be prepared as shown in Scheme 1. Compound I can be prepared through reaction of the corresponding primary amino compound, $R^1NH_2$, through heating with commercially available 6-chloroadenosine in the appropriate solvent (eg. n-butanol, dimethylformamide, and ethanol). The primary amino compound, $R^1NH_2$, is either commercially available or can be prepared as previously described in U.S. Pat. No. 5,789,416, the specification of which is incorporated herein by reference. The pro-drug esters of this invention can be prepared using all of the known methods for ester formation which are included by reference (see Jerry March Organic synthesis and Richard Larock—Methods of Organic Synthesis), and more preferably by those outlined in this application.

SCHEME 1

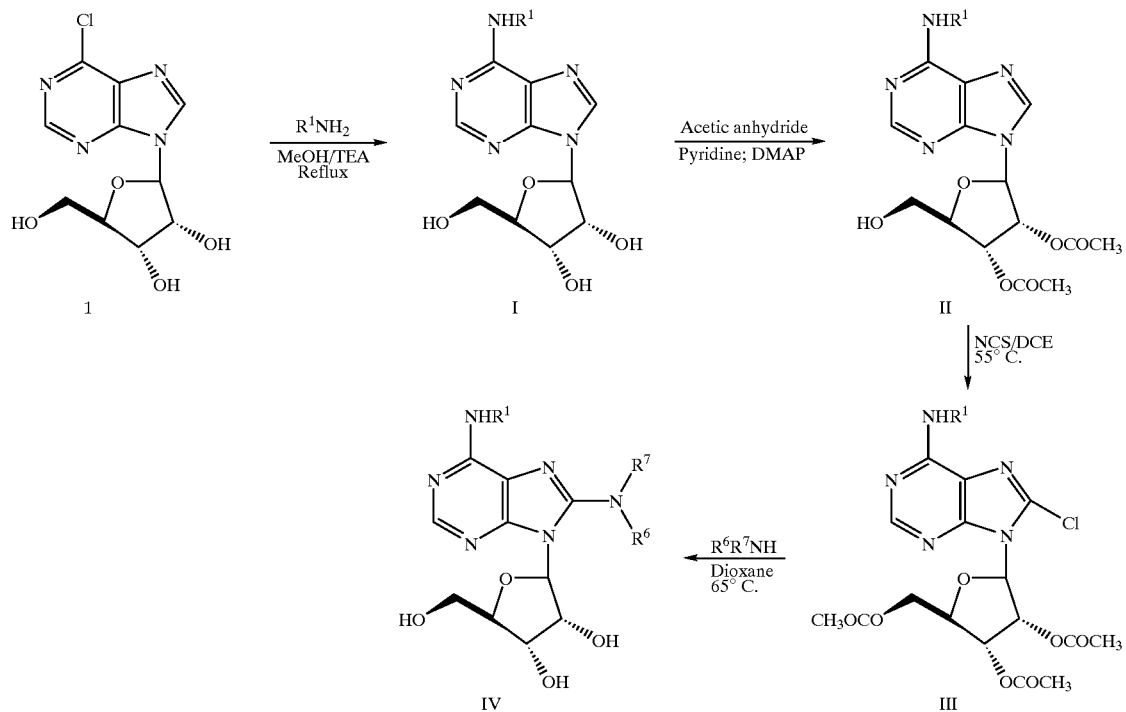

"Alkyl cycloalkyl" denotes the group —R—cycloalkyl where cycloalkyl is a cycloalkyl group and R is a lower alkyl or substituted lower alkyl. Cycloalkyl groups can optionally be unsubstituted or substituted with e.g. halogen, lower alkyl, lower alkoxy, alkylthio, acetylene, amino, amido, carboxyl, hydroxyl, aryl, aryloxy, heterocycle, substituted heterocycle, hetaryl, substituted hetaryl, nitro, cyano, thiol, sulfamido and the like.

"Alkyl cycloheteroalkyl" denotes the group —R-cycloheteroalkyl where R is a lower alkyl or substituted lower alkyl. Cycloheteroalkyl groups can optionally be unsubstituted or substituted with e.g. halogen, lower alkyl, lower alkoxy, alkylthio, amino, amido, carboxyl, acetylene, The key intermediate compound III can be prepared by the direct chlorination of the 2', 3', 5'-tri-O-acetyl-$N^6$-substitued adenosine (II). Compound II can be obtained by substitution of 6-chloropurine riboside with an amine (Fleysher, M. H. J. Med. Chem. 1972, 15, 187–191) followed by acetylation of the formed $N^6$-substituted adenosine (compound I). Nucleophilic displacement of the chlorine atom of compound III with different alkyl amines results in the formation of C-8 substituted compounds with simultaneous deacetylation to yield compound IV (HarlofRoelen et al. J. Med. Chem. 1996, 39, 1463–1471).

SCHEME 2
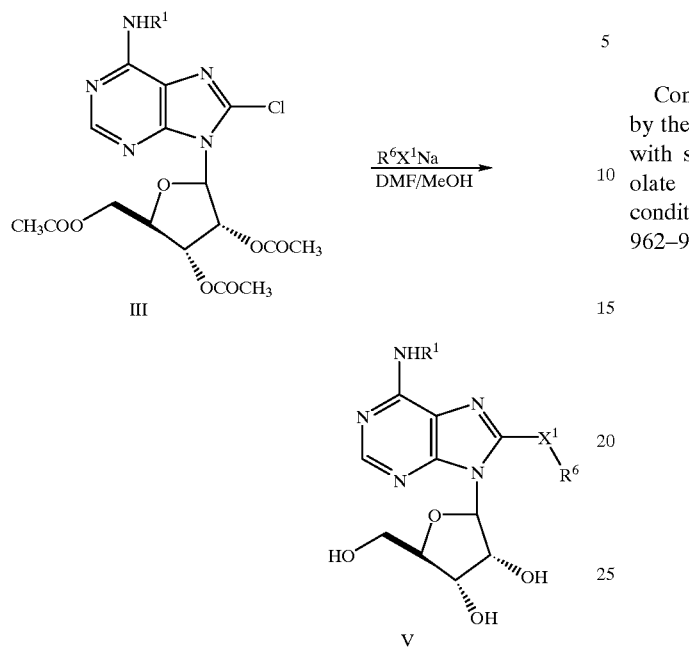
Compounds with the general structure V can be prepared by the reaction of compound III or compound I (scheme 1) with sodium aryloxide, alkoxide, arylthiolate or alkylthiolate in alcohol or DMF at room temperature or reflux conditions (G. Buenger and V. Nair, Synthesis, 1990, p 962–966).
SCHEME 3
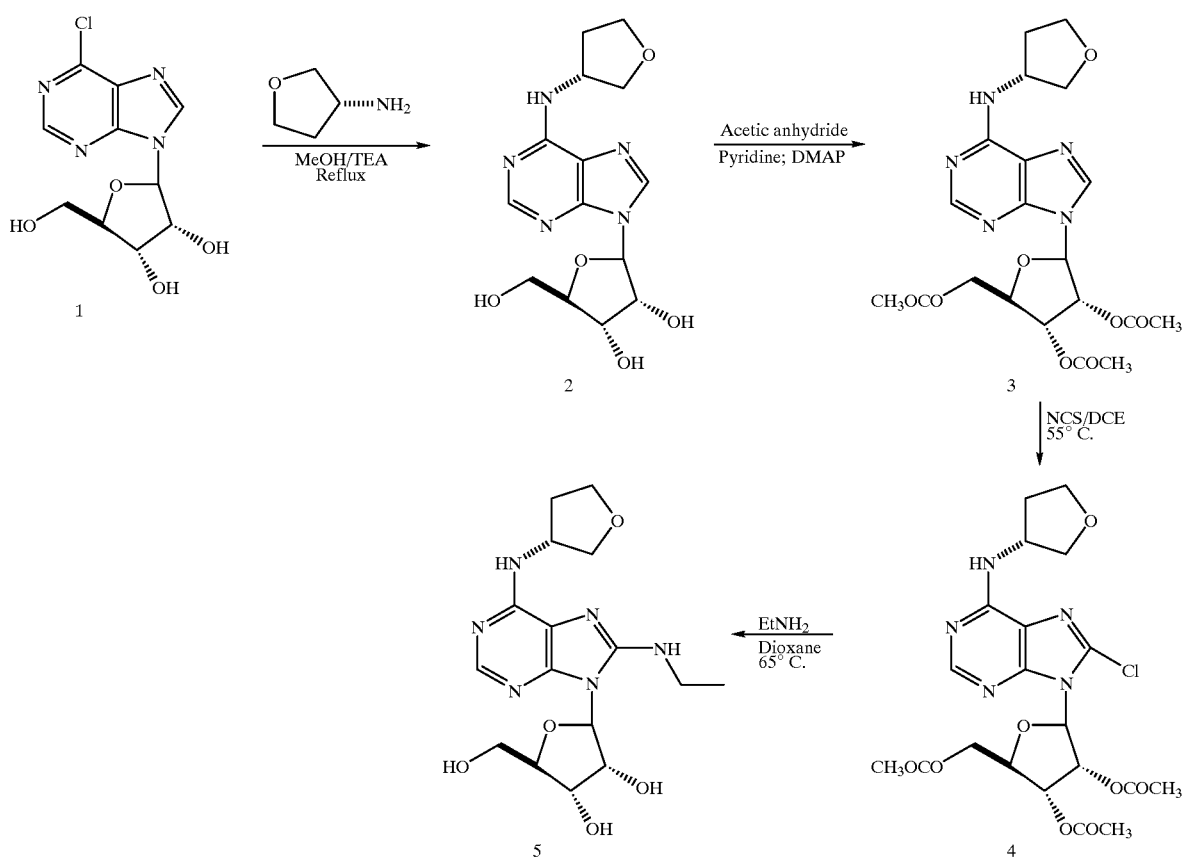

The preparation of compound 2 has been described previously in U.S. Pat. No. 5,789,416. Compound 4 has been obtained by the direct chlorination of compound 3 that has been prepared by the acetylation of compound 2. Nucleophilic displacement of the chlorine atom with ethylamine resulted in the formation of compound 5.

SCHEME 4

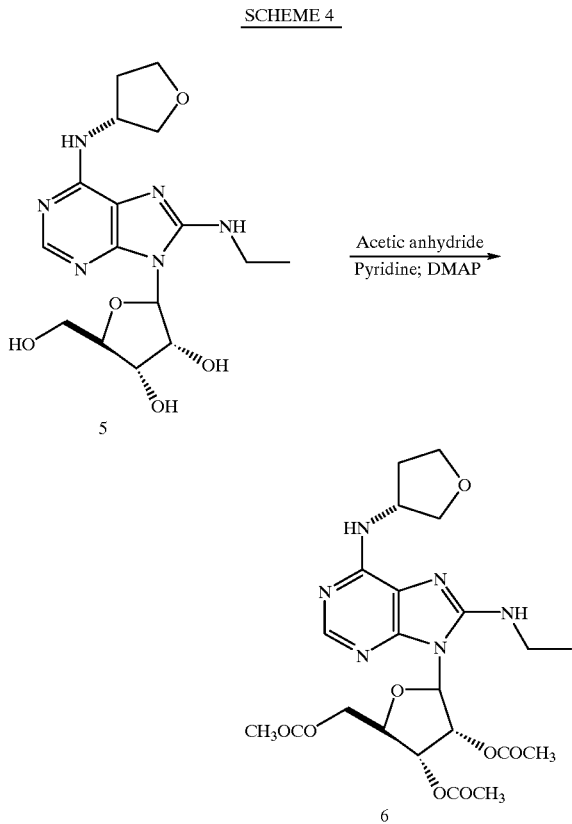

Compound 6 can be obtained by the direct acetylation of compound 5 (Scheme 4).

This invention also includes pro-drugs of the $A_1$ agonist compositions of this invention. A pro-drug is a drug which has been chemically modified and may be biologically inactive at its site of action, but which will be degraded or modified by one or more enzymatic or in vivo processes to the bioactive form. The pro-drugs of this invention should have a different pharmacokinetic profile to the parent enabling improved absorption across the mucosal epithelium, better salt formulation and/or solubility and improved systemic stability. The compounds of this invention may be preferably modified at one or more of the hydroxyl groups to form pro-drugs. The modifications may be (1) ester or carbamate derivatives which may be cleaved by esterases or lipases, for example; (2) peptides which may be recognized by specific or non specific proteinase; or (3) derivatives that accumulate at a site of action through membrane selection or a pro-drug form or modified pro-drug form, or any combination of (1) to (3) above.

If a compound of this invention contains a basic group, then corresponding acid addition salt may be prepared. Acid addition salts of the compounds are prepared in a standard manner in a suitable solvent from the parent compound and an excess of acid, such as hydrochloric, hydrobromic, sulfuric, phosphoric, acetic, maleic, succinic, or methanesulfonic. The hydrochloric salt form is especially useful. If a compound of this invention contains an acidic group, then corresponding cationic salts may be prepared. Typically the parent compound is treated with an excess of an alkaline reagent, such as hydroxide, carbonate or alkoxide, containing the appropriate cation. Cations such as $Na^+$, $K^+$, $Ca^{+2}$ and $NH_4^+$ are examples of cations present in pharmaceutically acceptable salts. Certain of the compounds form inner salts or zwitterions which may also be acceptable.

The compositions of this invention are useful for treating a variety of mammalian disorders and preferably human disorders that are mediated by an $A_1$ adenosine receptor. For example, the compositions of this invention are useful for modifying cardiac activity in mammals experiencing a coronary electrical disorder that can be treated by stimulating an $A_1$ adenosine receptor. Examples of coronary electrical disorders that can be treated by the compositions of this invention include supraventricular tachycardias, atrial fibrillation, atrial flutter, and AV nodal re-entrant tachycardia. Furthermore, orally active $A_1$ agonists of this invention that demonstrate an excellent safety profile in treating supraventricular arrhythmias may also be used as a prophylactic for those at high risk of a myocardial ischemia.

The compositions of this invention are also useful for modifying adipocyte function by stimulating an $A_1$ adenosine receptor that leads to diminished release of NEFA and increased release of leptin. Disease states related to adipocyte function that can be modified using compositions of this invention include diabetes, and obesity.

In skeletal muscle cells, $A_1$ AdoR agonists mediate a synergistic stimulation of glucose uptake and transport by insulin (Vergauwen, L. et al, *J. Clin. Invest.* 1994, 93, 974–81; Challiss, R. A. et al, *Eur. J. Pharacol.,* 1992, 226, 121–8). Another therapeutic utility of compositions of this invention is more efficient regulation of glucose and a decrease of circulating levels of insulin in patients afflicted with diabetes.

The $A_1$ receptor agonist, R-PIA, has been shown to increase the leptin released from white adipocytes and augment insulin-stimulated leptin production (M. Ozeck Master's Thesis Univ. of Florida 1999 with L. Belardinelli). Evidence suggests that catecholamines inhibit the production of leptin from adipocytes through activation of β-adrenergic receptors. The anti-β-adrenergic effects of $A_1$ agonists on the adipocytes are believed to play a role in the increased release of leptin. The functional role of leptin is multifaceted including decreased appetite, stimulated energy utilization, and increased fertility.

The compositions of this invention may also be used to provide central nervous system neuroprotection by stimulating an $A_1$ adenosine receptor. Central nervous system disorders that may be treated using the compositions of this invention include epilepsy, and stroke.

In the kidney, there is evidence that stimulation of the $A_1$ AdoR promotes sodium retention, promotes exchange of sodium in urine for potassium, and reduces glomerular filtration rate as sodium excretion increases (Gellai, M. et al, JPET, 1998, 286, 1191–6; Wilcox, C. S. et al, *J. Am. Soc. Nephrol.,* 1999, 10, 714–720). It is believed that these responses are elicited by chronic local production of adenosine. That is, in the kidney there is a tonic effect of adenosine to stimulate the $A_1$ AdoR. Another clinical utility of compositions of this invention, therefore, is the selective antagonism of the $A_1$ AdoR in the kidney to inhibit sodium retention, inhibit the exchange of sodium for potassium, and preserve kidney glomerular filtration rate when sodium excretion rises to yield a potassium sparring diuretic that preserves renal fumction.

The compositions of this invention are further useful for providing cardiomyocyte protection from ischemic events by stimulating an $A_1$ adenosine receptor. Ischemic events treatable using the compositions of this invention include stable angina, unstable angina, cardiac transplant, and myocardial infarction.

An important aspect of compounds of this invention is that each compound has an intrinsic efficacy associated with it (for a discussion see T. P. Kenakin Stimulus Response Mechanisms. In Pharmacological Analysis of Drug-Receptor Interaction, Ed. Kenakin, T. P. New York: Raven Press, p 39–68). This intrinsic efficacy is not defined by it's affinity for the receptor, but it is defined as the quantitative effect of the compound to activate a given effector system (eg. cAMP production) in a given cell type. The intrinsic efficacy of a given compound may vary from cell type to cell type and/or from effector system to effector system. When a compound has an intrinsic efficacy lower than a full agonist (i.e. submaximal) than the agonist is called a partial agonist. Thus, a partial agonist is a molecule that binds to a receptor and elicits a response that is smaller than that of a full agonist (submaximal), but also competitively antagonizes the response(s) elicited by a full agonist. The tonic action of adenosine with resepct to kidney function is a prime example where a partial $A_1$ agonist be expected to act as antagonists (e.g. adenosine). The tonic action of adenosine with respect to kidney function is a prime example where a partial $A_1$ agonist could be expected to act as an antagonist. The compounds of this invention are believed to have therapeutically useful affinities for the adenosine $A_1$ receptor, and they will have a range of intrinsic efficacies from full agonist to partial agonist. That is, some compounds may have no effect with respect to a given effector system in a given cell type, but be a full agonist in another cell type and/or effector system. The reason for such variable pharmacological behavior relates to the magnitude of the receptor reserve for the $A_1$ adenosine receptor in any given cell type (eg. AV nodal cells vs. adipocytes) and for a given response. The receptor reserve (spare receptor capacity) is the total number of receptors minus the fraction of receptors that is required to induce the maximal response using a fall agonist (L. E. Limbird, Cell Surface Receptors: A Short Course on Theory and Methods, Kluwer Acad. Pub. 1996, Boston, Mass.). Therefore, the agonist could be a full agonist at eliciting a response, and a partial agonist for eliciting another response in other tissue or cells and still be an antagonist or lack activity for a third response in another tissue or cell. Consequently, a partial agonist targeted to a selected target is likely to cause fewer side effects than a full agonist. As a corollary, a full agonist elicits all the effects mediated by the respective receptor, whereas this is not necessarily the case of a partial agonist. The compounds of this invention based on their affinity for the $A_1$ receptor and their potency and selectivity to elicit $A_1$ receptor mediated responses have the potential for therapeutic intervention in the multiple disease states described above.

Partial $A_1$ agonists may have an added benefit for chronic therapy because they will be less likely to induce desensitization of the $A_1$ receptor (R. B. Clark, B. J. Knoll, R. Barber TiPS, Vol. 20 (1999) p. 279–286) and to cause side effects. Chronic administration of a full agonist (R-N6-phenylisopropyladenosine, R-PIA) for 7 days led to a desensitization of the $A_1$ receptor in terms of the dromotropic response in guinea pigs (note: a decrease in receptor number was observed—D. M. Dennis, J. C. Shryock, L. Belardinelli JPET, Vol. 272 (1995) p. 1024–1035). The $A_1$ agonist induced inhibitory effect on the production of cAMP by adenylate cyclase in adipocytes has been shown to desensitize upon chronic treatment with an $A_1$ agonist as well (W. J. Parsons and G. L. Stiles J. Biol. Chem. Vol. 262 (1987) p. 841–847).

The compositions of this invention may be administered orally, intravenously, through the epidermis, bolus, nasally, by inhalation or by any other means known in the art for administering a therapeutic agents. The method of treatment comprises the administration of an effective quantity of the chosen compound, preferably dispersed in a pharmaceutical carrier. Dosage units of the active ingredient are generally selected from the range of 0.01 to 100 mg/kg, but will be readily determined by one skilled in the art depending upon the route of administration, age and condition of the patient.

Pharmaceutical compositions including the compounds of this invention, and/or derivatives thereof, may be formulated as solutions or lyophilized powders for parenteral administration. Powders may be reconstituted by addition of a suitable diluent or other pharmaceutically acceptable carrier prior to use. If used in liquid form the compositions of this invention are preferably incorporated into a buffered, isotonic, aqueous solution. Examples of suitable diluents are normal isotonic saline solution, standard 5% dextrose in water and buffered sodium or ammonium acetate solution. Such liquid formulations are suitable for parenteral administration, but may also be used for oral administration. It may be desirable to add excipients such as polyvinylpyrrolidinone, gelatin, hydroxycellulose, acacia, polyethylene glycol, mannitol, sodium chloride, sodium citrate or any other excipient known to one of skill in the art to pharmaceutical compositions including compounds of this invention. Alternatively, the pharmaceutical compounds may be encapsulated, tableted or prepared in an emulsion or syrup for oral administration. Pharmaceutically acceptable solid or liquid carriers may be added to enhance or stabilize the composition, or to facilitate preparation of the composition. Liquid carriers include syrup, peanut oil, olive oil, glycerin, saline, alcohols and water. Solid carriers include starch, lactose, calcium sulfate, dihydrate, teffa alba, magnesium stearate or stearic acid, talc, pectin, acacia, agar or gelatin. The carrier may also include a sustained release material such as glycerol monostearate or glycerol distearate, alone or with a wax. The amount of solid carrier varies but, preferably, will be between about 20 mg to about 1 gram per dosage unit. The pharmaceutical dosages are made using conventional techniques such as milling, mixing, granulation, and compressing, when necessary, for tablet forms; or milling, mixing and filling for hard gelatin capsule forms. When a liquid carrier is used, the preparation will be in the form of a syrup, elixir, emulsion or an aqueous or non-aqueous suspension. Such a liquid formulation may be administered directly or filled into a soft gelatin capsule.

The Examples which follow serve to illustrate this invention. The Examples are intended to in no way limit the scope of this invention, but are provided to show how to make and use the compounds of this invention.

EXAMPLE 1

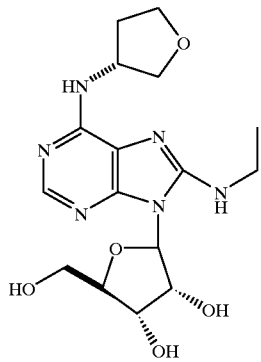

2-{6-[((3R)oxolan-3-yl)amino]-8-(ethylamino)purin-9-yl}(4S,2R,3R,5R)-5-(hydroxymethyl)oxolane-3,4-diol (Compound 5)

5-{6-[((3R)oxolan-3-yl)amino]purin-9-yl}(4S,2R,3R,5)-4-acetoxy-2-(acetoxymethyl)oxolane-3yl-acetate: 2-{6-[((3R)oxolan-3-yl)amino]purin-9-yl}(4S,2R,3R,5R)-5-(hydroxymethyl) oxolane-3,4-diol (2) was prepared from 6-Chloro purine riboside as described in U.S. Pat. No. 5,789,416, the specification of which is incorporated herein by reference. To a solution of compound 2 (1.68 g, 5 mmol) and dimethylaminopyridine (100 mg, 0.82 mmol) in pyridine (10 mL) at 23° C. was added acetic anhydride (1 mL, 10.6 mmol). After 3 h at 23° C., the reaction was concentrated in vacuo. The residue was dissolved in methylene chloride (100 mL), washed with water (3×20 mL), and dried (Na$_2$SO$_4$). After concentration in vacuo, the residue was purified by flash chromatography (methylene chloride: methanol 20:1 followed by 9:1) to afford compound 3.

Synthesis of 5-{6-[((3R)oxolan-3-yl)amino]-8-chloropurin-9-yl}(4S,2R,3R5R)-4-acetoxy-2-(acetoxymethyl)oxolane-3yl-acetate: To a stirred solution of compound 3 (1 g, 2.16 mmol) in 1,2-dichloroethane (10 mL) was added N-chlorosuccinimide (1 g, 7.5 mmol) and the reaction was warmed to 55° C. for 24 h. The solvent was evaporated and the product purified by flash chromatography (methylene chloride: methanol 100:0 followed by 95:5) to afford compound 4.

To a stirred solution of compound 4 (100 mg, 0.2 nimol) in dioxane (0.5 mL) ethylamine (75% aqueous solution, 3 mL) was added and the reaction was warmed to 65° C. for 16 h. The resulting mixture was evaporated to dryness and the product purified by preparative TLC using methylene chloride:methanol (95:5) as solvent to afford compound 5: $^1$H NMR (CD$_3$OD)δ1.25(τ, 3H), 1.80–1.90(m, 1H), 2.30–2.40 (m, 1H), 3.40 (q, 2H), 3.50–3.90 (m, 4H), 3.90–4.00 (m,2H), 4.10–4.15 (m, 1H), 4.20–4.25 (m, 1H), 4.65–4.80 (m, 2H), 5.95 (d, 1H), 7.95 (s, 1H). [MS: 381.25 (M+1)].

EXAMPLE 2

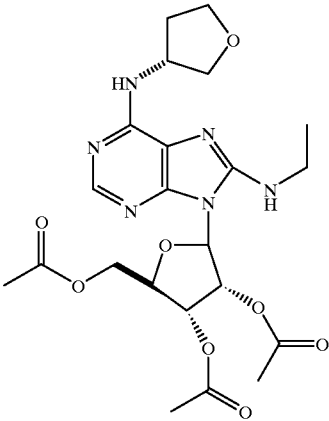

(6)

(5-{6-[((3R)oxolan-3-yl)amino]-8-(ethylamino)purin-9-yl}(2R,3R,4R,5R)-3,4-diacet yloxyoxolan-2-yl)methyl acetate (compound 6)

Compound 6 was prepared (Scheme 4) as described for the synthesis of compound 3 in Example 1, above.

$^1$HNMR (CDCl$_3$) δppm: 1.28 (t, 3H), 1.95 (m, 1H), 1.99 (s, 3H), 2.09 (s, 3H), 2.11 (s, 3H), 2.45 (m, 1H), 3.46 (m, 2H), 3.81 (m, 2H), 3.98 (m, 2H), 4.32 (m, 2H), 5.45 (d, 1H), 5.61 (d, 1H), 5.78 (t, 1H), 6.12 (d, 1H), 8.18 (s, 1H).

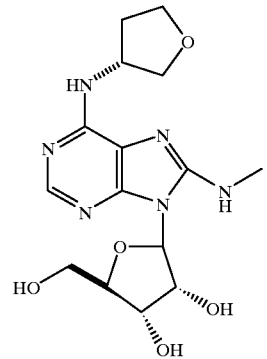

2-{6-[((3R)oxolan-3-yl)amino]-8-(methylamino)purin-9-yl}(4S,2R,3R,5R)-5-(hydroxymethyl)oxolane-3,4-diol (compound 7)

Compound 7 was prepared as described in example 1 substituting methylamine for thylamine: $^1$H NMR (CDCl$_3$) δ1.75–1.85(m, 1H), 2.10–2.25(m, 1H), 2.8 (s, 3H), 3.60–3.70 (m, 2H), 3.70–3.80 (m, 2H), 3.80–3.90(m, 2H), 4.00–4.05 (m, 1H), 4.10–4.15 (m, 1H), 4.50–4.55 (m, 2H), 5.7 (d, 1H), 6.5–6.5(m, 1H), 7.9 (s, 1H).

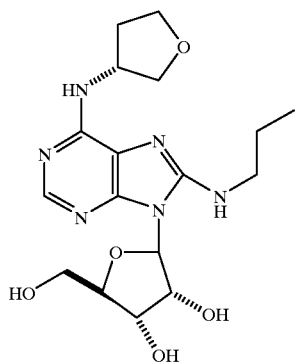

2-{6-[((3R)oxolan-3-yl)amino]-8-(propylamino)purin-9-yl}(4S,2R,3R,5R)-5-(hydroxymethyl)oxolane-3,4-diol (compound 8)

Compound 8 was prepared as described in example 1 substituting n-propylamine for ethylamine: $^1$H NMR (CDCl$_3$) δ0.85 (t, 3H), 1.50–1.60(u, 2H), 1.80–1.90(m, 1H), 2.20–3.20 (t, 2H), 3.60–3.70 (m, 2H), 3.70–4.00 (m,4H), 4.05–4.10 (m, 1H), 4.10–4.15 (m, 1H), 4.50–4.60 (m, 2H), 5.75 (d, 1H), 6.50–6.60(m, 1H), 7.95 (s, 1H).

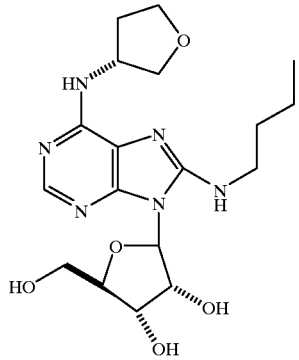

2-{6-[((3R)oxolan-3-yl)amino]-8-(butylamino)purin-9-yl}(4S,2R,3R,5R)-5-(hydroxymethyl)oxolane-3,4-diol (compound 9)

Compound 9 was prepared as described in example 1 substituting n-butylamine for ethylamine: $^1$H NMR (CDCl$_3$) δ0.80 (π, 3H), 1.15–1.40(m, 4H), 1.90–2.00(m, 1H), 2.85–2.95 (m, 2H), 3.70–3.90 (m, 5H), 4.00–4.05 (m, 1H), 4.20–4.25 (m, 1H), 4.60–4.65 (m, 1H), 4.90–4.95 (m, 1H), 5.50 (bs, 1H), 5.80 (d, 1H), 6.2 (bs, 2H), 7.95 (s, 1H).

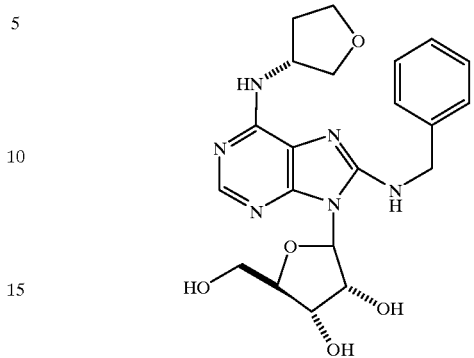

2-{6-[((3R)oxolan-3-yl)amino]-8-[benzylamino]purin-9-yl}(4S,2R,3R,5R)-5-(hydroxymethyl)oxolane-3,4-diol (compound 10)

Compound 10 was prepared as described in example 1. Substituting benzylamine for ethylamine: $^1$H NMR (CDCl$_3$) δ1.80–1.90 (m, 1H), 2.15–2.25 (m, 1H), 3.60–3.70 (m, 2H), 3.70–3.80 (m,2H), 3.90 (q,2H), 4.05–4.10 (m, 1H), 4.20–4.30 (m, 1H), 4.30–4.40 (m, 1H), 4.60–4.70 (m, 1H), 4.85–4.95 (m, 1H), 5.80 (d, 1H), 6.05–6.10 (m, 1H), 6.15–6.20 (m, 1H), 6.30–6.50(m, 1H), 7.15–7.30 (m, 5H), 7.95 (s, 1H).

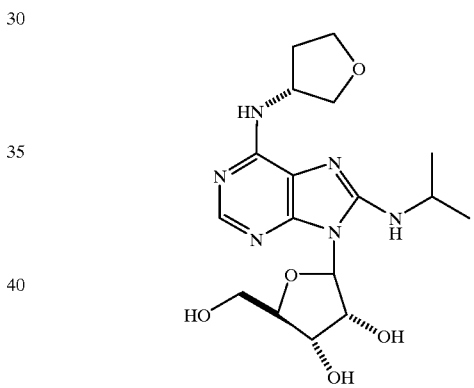

2-{6-[((3R)oxolan-3-yl)amino]-8-[(methylethyl)amino]purin-9-yl}(4S,2R,3R,5R)-5-(hydroxymethyl)oxolane-3,4-diol (compound 11)

Compound 11 was prepared as described in example 1 substituting isopropylamine for ethylamine[MS: 395.30 (M+1)]

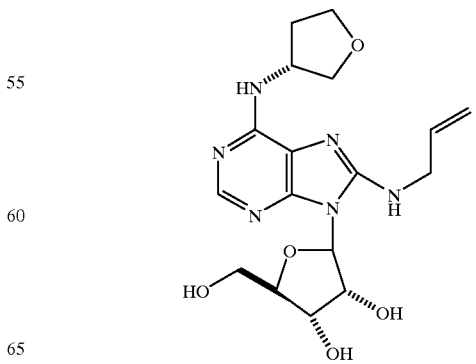

2-{6-[((3R)oxolan-3-yl)amino]-8-(prop-2-enylamino)purin-9-yl}(4S,2R,3R,5-(hydroxymethyl)oxolane-3,4-diol (compound 12)

Compound 12 was prepared as described in example 1 substituting allylamine for ethylamine [(MS: 393.7 (M+1)].

EXAMPLE 3

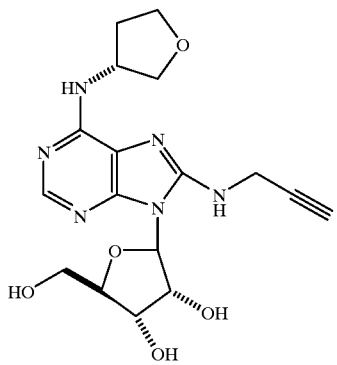

2-{6-[((3R)oxolan-3-yl)amino]-8-(prop-2-ynylamino)purin-9-yl}(4S,2R,3R,5R)5-(hydroxymethyl)oxolane-3,4-diol (compound 13)

Compound 13 was prepared as described in example 1 substituting propargylamine for ethylamine[MS: 391.37 (M+1)].

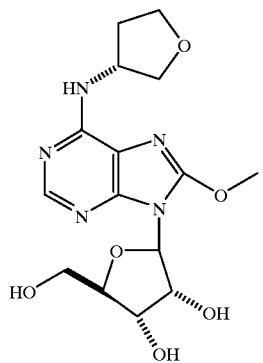

2-{6-[((3R)oxolan-3-yl)amino]-8-methoxypurin-9-yl}(4S,2R,3R,5R)-5-(hydroxymethyl)oxolane-3,4-diol (compound 13)

To a solution of compound 4 in 1 mL of dry methanol was added 3 mL of 0.5M solution of sodium methoxide in methanol. The reaction mixture was refluxed for 30 min. TLC (5% MeOH: 95% DCM) showed that the reaction was completed. The reaction mixture was cooled and quenched with a few drops of glacial acetic acid and the solvent was evaporated. The residue was taken up in methanol and analyzed by mass spectrometer [MS 368.2 (M+1) and 390.2 (M+23)].

EXAMPLE 4

Binding Assays—$DDT_1$ Cells

Cell Culture

DDT cells (hamster vas deferens smooth muscle cell line) were grown as monolayers in petri dishes using Dulbecco's Modified Eagle's Medium (DMEM) containing 2.5 μg ml$^{-1}$ amphotericin B, 100 U ml$^{-1}$ penicillin G, 0.1 mg ml$^{-1}$ streptomycin sulfate and 5% fetal bovine serum in a humidified atmosphere of 95% air and 5% $CO_2$. Cells were subcultured twice weekly by dispersion in Hank's Balanced Salt Solution (HBSS) without the divalent cations and containing 1 mM EDTA. The cells were then seeded in growth medium at a density of $1.2 \times 10^5$ cells per plate and experiments were performed 4 days later at approximately one day preconfluence.

Membrane Preparations

Attached cells were washed twice with HBSS (2×10 ml), scraped free of the plate with the aid of a rubber policeman in 5 ml of 50 mM Tris-HCl buffer pH 7.4 at 4° C. and the suspension homogenized for 10 s. The suspension was then centrifuged at 27,000×g for 10 min. The pellet was resuspended in homogenization buffer by vortexing and centrifuged as described above. The final pellet was resuspended in 1 vol of 50 mM Tris-HCl buffer pH 7.4 containing 5 mM $MgCl_2$ for $A_1$ AdoR assays. For the [$^{35}$S]GTPγS binding assay the final pellet was resuspended in 50 mM Tris-HCl pH 7.4 containing 5 mM $MgCl_2$, 100 mM NaCl and 1 mM dithiothreitol. This membrane suspension was then placed in liquid nitrogen for 10 min, thawed and used for assays. The protein content was determined with a Bradford™ Assay Kit using bovine serum albumin as standard.

Competitive Binding Assay

Pig striatum were prepared by homogenation in 50 mM Tris buffer ( 5×volume of tissue mass pH=7.4). After centrifugation at 19,000 rpm for 25 minutes at 4° C., the supernatant was discarded, and the process was repeated twice. Compositions of this invention were assayed to determine their affinity for the $A_1$ receptor in a pig striatum membrane prep or a $DDT_1$ membrane prep. Briefly, 0.2 mg of pig striatal membranes or $DDT_1$ cell membranes were treated with adenosine deaminase and 50 mM Tris buffer (pH=7.4) followed by mixing. To the pig membranes was added 2 μL of serially diluted DMSO stock solution of the compounds of this invention at concentrations ranging from 100 microM to 10 nM. The control received 2 microL of DMSO alone, then the antagonist [$^3$H] 8-cyclopentylxanthine (CPX) for pig striatum or the agonist [$^3$H] 2-chloro-6-cyclopentyladenosine (CCPA) for $DDT_1$ membranes in Tris buffer (50 mM, pH of 7.4) was added to achieve a final concentration of 2 nM. After incubation at 23 C. for 2 h, then the solutions were filtered using a membrane harvester using multiple washing of the membranes (3×). The filter disks were counted in scintillation cocktail affording the amount of displacement of tritiated CPX or by the competitive binding compositions of this invention. Greater than a 5 point curve was used to generate Ki's and the number of experiments is indicated in the column marked in Table 1, below:

TABLE 1

| Compound # | $K_i$ - $DDT_1$ cell membrane | $K_i$ - Pig Striatum |
|---|---|---|
| 5 | 171 nM | 137 nM |
| 7 | — | 799 nM |
| 8 | — | 1040 nM |
| 9 | — | 2840 nM |
| 10 | — | 7470 nM |

EXAMPLE 5

[$^{35}$S]GTPγS Binding Assays $A_1$-agonist stimulated [$^{35}$S] GTPγS binding was determined by a modification of the method described by Giersckik et al. (1991) and Lorenzen et al. (1993). Membrane protein (30–50 μg) was incubated in a volume of 0.1 ml containing 50 mM Tris-HCl buffer pH 7.4, 5 mM $MgCl_2$, 100 mM NaCl, 1 mM dithiothreitol, 0.2 units ml$^{-1}$ adenosine deaminase, 0.5% BSA, 1 mM EDTA, 10 mM GDP, 0.3 nM [$^{35}$S]GTPγS and with or without varying concentrations of CPA for 90 min at 30° C. Nonspecific binding was determined by the addition of 10 μM GTPγS. Agonist stimulated binding was determined as the difference between total binding in the presence of CPA and basal binding determined in the absence of CPA. Previous reports have shown that agonist stimulated [$^{35}$S]GTPγS binding was dependent on the presence of GDP (Gierschik et al., 1991; Lorenzen et al., 1993; Traynor & Nahorski, 1995). In preliminary experiments, it was found that 10 μM GDP gave the optimal stimulation of CPA dependent [$^{35}$S]GTPγS binding and this concentration was therefore used in all studies. In saturation experiments, 0.5 nM [$^{35}$S]GTPγS was incubated with 0.5–1000 nM GTPγS. At the end of the incubation, each suspension was filtered and the retained radioactivity determined as described above. Results are presented normalized to the full agonist N-6-cyclopentyladenosine, CPA.

TABLE 2

| Compound # | GTPγS |
|---|---|
| CPA | 100% |
| 5 | 89% |
| 11 | 68% |
| 12 | 77% |
| 13 | 95% |

EXAMPLE 6 cAMP Assay

A scintillation proximity assay (SPA) using rabbit antibodies directed at cAMP using an added tracer of adenosine 3',5'-cyclic phosphoric acid 2'-O-succinyl-3-[$^{125}$I] iodotyrosine methyl ester and fluoromicrospheres containing anti-rabbit specific antibodies as described by Amersham Pharmacia Biotech (Biotrak cellular communication assays). Briefly, $DDT_1$ cells were cultured in clear bottomed 96 well microtiter plates with opaque wells at concentrations between $10^4$ to $10^6$ cells per well in 40 μl of HBSS at 37° C. (5% $CO_2$ and 95% humidity). The partial or full $A_1$ agonists (5 μl) of this invention were incubated at various concentrations with the $DDT_1$ cells in the presence of rolipram (50 μM), and 5 μM forskolin for 10 min at 37° C. The cells were immediately lysed by treatment 5 μl of 10% dodecyltrimethylammonium bromide followed by shaking using microplate shaker. After incubation of the plate for 5 minutes, an immunoreagent solution (150 μl containing equal volumes of tracer, antiserum, and SPA fluorospheres) was added to each well followed by sealing the plate. After 15–20 h at 23° C., the amount of bound [125I] cAMP to the fluoromicrospheres was determined by counting in a microtitre plate scintillation counter for 2 minutes. Comparison of counts with standard curves generated for cAMP using a similar protocol afforded the cAMP present after cell lysis. Results are presented normalized to the full agonist N-6-cyclopentyladenosine, CPA. Thus, the full agonist CPA diminished the amount of forskolin induced cAMP generation back to basal levels.

TABLE 3

| Compound # | cAMP |
|---|---|
| CPA | 100% |
| 11 | 37% |

TABLE 3-continued

| Compound # | cAMP |
|---|---|
| 12 | 42% |
| 13 | 41% |

What we claim is:

1. A compound having the formula:

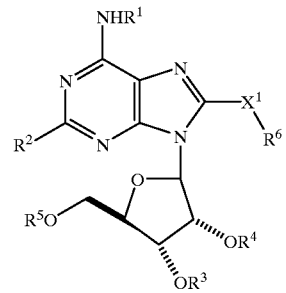

wherein $X^1$=O, or —$NR^7$;

$R^1$ is a monocyclic group containing from 3 to 15 atoms wherein at least one carbon atom is substituted with an atom or molecule selected from the group consisting of O and S—(O)$_{0-2}$ and wherein $R^1$ is optionally mono or polysubstituted with one or more substituent selected from the group consisting of halogen, oxo, hydroxyl, lower alkyl, substituted lower alkyl, alkoxy, aryl, acyl, aryloxy, carboxyl, substituted aryl, heterocycle, heteroaryl, substituted heteroaryl, cycloalkyl, substituted cycloalkyl, nitro, and cyano;

$R^2$ is hydrogen;

$R^3$, $R^4$, and $R^5$ are each individually selected from the group consisting of hydrogen, —(CO)—R', —(CO)—R'', and —(CO)—R''' wherein R', R'', and R''' are each independently selected from the group consisting of $C_{1-6}$ alkyls which alkyl is optionally substituted with 1 substituent selected from the group consisting of aryl, $CF_3$, CN, $OR^{20}$, and $N(R^{20})_2$, and each optional aryl substituent is further optionally substituted with halo, $NO_2$, alkyl, or $CF_3$;

$R^6$ is selected from the group consisting of hydrogen, and $C_{1-3}$ alkyls;

$R^7$ is selected from the group consisting of hydrogen, $C_{1-6}$ alkyls, $C_{3-6}$ alkenyls, and $C_{3-6}$ alkynyls, wherein the alkenyl and alkynyl point of attachment is not at an unsaturated carbon and wherein the alkyl, alkenyl, and alkynyl substituents are optionally substituted with from 1 to 2 substituents independently selected from the group consisting of alkyl, aryl, $CF_3$, $OR^{20}$, $SR^{20}$, $CO_2R^{20}$, and $S(O)_3R^{20}$, wherein each optional aryl substituent is further optionally substituted with a substituent selected from the group consisting of halo, alkyl, $CF_3$, $S(O)_3R^{20}$, $CO_2R^{20}$, amino, mono- or di-alkylamino, CN, and $OR^{20}$; and $R^{20}$ is selected from the group consisting of H, and $C_{1-6}$ alkyl.

2. The compound of claim 1 wherein $X^1$=$NR^7$;

$R^2$ is hydrogen;

$R^3$, $R^4$, and $R^5$ are independently selected from the group consisting of hydrogen, —(CO)—R', —(CO)—R'', and —(CO)—R''' wherein R', R'', and R''' are independently selected from the group consisting of $C_{1-6}$ alkyls;

$R^6$ is independently selected from the group consisting of hydrogen, and $C_{1-3}$ alkyls;

$R^7$ is independently selected from the group consisting of hydrogen, $C_1$ alkyls, $C_{3-6}$ alkenyls, and $C_{3-6}$ alkynyls, wherein the alkenyl and alkynyl point of attachment is not at an unsaturated carbon and wherein the alkyl, alkenyl, and alkynyl substituents are optionally substituted with 1 substituent optionally selected from the group consisting of alkyl, aryl, $CF_3$, $OR^{20}$, $SR^{20}$, $CO_2R^{20}$, and $S(O)_3R^{20}$, and wherein optional aryl substituent is optionally substituted with halo, alkyl, or $CF_3$; and $R^{20}$ is a member selected from the group consisting of H, and $C_{1-6}$ alkyl.

3. The compound of claim 1 wherein $X^1$=$NR^7$;

$R^2$ is hydrogen;

$R^3$, $R^4$, and $R^5$ are independently selected from the group consisting of hydrogen, —(CO)—R', —(CO)—R", and —(CO)—R'" wherein R', R", and R'" are independently selected from the group consisting of $C_{1-3}$ alkyls;

$R^6$ is hydrogen; and $R^7$ is independently selected from the group consisting of hydrogen, $C_{1-6}$ alkyls, $C_{3-6}$ alkenyls, and $C_{3-6}$ alkynyls, wherein the alkenyl and alkynyl point of attachment is not at an unsaturated carbon and wherein the alkyl, alkenyl, and alkynyl substituents are optionally substituted with 1 substituent optionally selected from the group consisting of alkyl and aryl.

4. The compound of claim 1 wherein $X^1$=$NR^7$;

$R^2$ is hydrogen;

$R^3$, $R^4$, and $R^5$ are each independently selected from the group consisting of hydrogen, —(CO)—R', —(CO)—R", and —(CO)—R'" wherein R', R", and R'" are each methyl;

$R^6$ is hydrogen;

$R^7$ is selected from the group consisting of hydrogen, $C_{1-6}$ alkyls, $C_{3-6}$ alkenyls and $C_{3-6}$ alkynyls, wherein the alkenyl and alkynyl point of attachment is not at an unsaturated carbon and wherein the alkyl, alkenyl, and alkynyl substituents are optionally substituted with 1 substituent selected from the group consisting of alkyl and aryl.

5. The compound of claim 1 wherein $X^1$=$NR^7$;

$R^2$ is hydrogen;

$R^3$ $R^4$, $R^5$ and $R^6$ are each hydrogen; and $R^7$ is independently selected from the group consisting of hydrogen, $C_{1-6}$ alkyls, $C_{3-4}$ alkenyls, and $C_{3-4}$ Sibyls wherein the alkenyl and alkynyl point of attachment is not at an unsaturated carbon and wherein the alkyl, alkenyl, and alkynyl substituents are optionally substituted with 1 substituent selected from the group consisting of alkyl and aryl.

6. The compound of claim 1 wherein $R^1$ is mono or polysubstituted with one or more compounds selected from the group consisting of halogen, oxo, hydroxyl, lower alkyl, substituted lower alkyl, alkoxy, aryl, acyl, aryloxy, carboxyl, substituted aryl, heterocycle, heteroaryl, substituted heteroaryl, cycloalkyl, substituted cycloalkyl, nitro, cyano and mixtures thereof.

7. The compound of claim 1 selected from the group consisting of $N^6$-{3-(3R)tetrahydrofuranyl}-8-isopropylaminoadenosine, $N^6$-{3-(3R)tetrahydrofuranyl}-8-(2-propyl)aminoadenosine, $N^6$-{3-(3R)tetrahydrofuranyl}-8-allylaminoadenosine, $N^6$-{3-(3R)tetrahydrofuiranyl}-8-(2-propenyl)aminoadenosine, $N^6$-{3-(3R) tetrahydroftiranyl}-8-ethylaminoadenosine, $N^6$-{3-(3R) tetrahydrofuranyl}-8-propylaminoadenosine, $N^6$-{3-(3R) tetrahydrofuranyl}-8-butylaminoadenosine, $N^6$-{3-(3R) tetrahydrofuranyl}-8-benzylaminoadenosine, $N^6$-{3-(3R) tetrahydrofuranyl}-8-methylaminoadenosine, and $N^6$-{3-(3R)tetrahydrofiiranyl}-8-isopropylamino-2',3',5'-tri-O-acetyladenosine.

8. The compound of claim 1 wherein $R_1$ is:

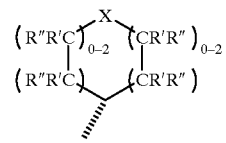

wherein X is O, or S $(-O)_{0-2}$ and R' and R" are individually selected from the group consisting of hydrogen, halogen, hydroxyl, lower alkyl, substituted lower alkyl, alkoxy, aryl, acyl, aryloxy, carboxyl, substituted aryl, heterocycle, heteroaryl, substituted heteroaryl, cycloalkyl, substituted cycloalkyl nitro, and cyano, and alternatively CR'R' may be C=O.

9. The compound of claim 8 wherein R' and R" are each individually selected from the group consisting of hydrogen, lower alkyl, and substituted lower alkyl and wherein X is O.

10. The compound of claim 8 wherein R' and R" are individually selected from the group consisting of hydrogen lower alkyl, substituted lower alkyl, alkoxy, aryl, and substituted aryl.

11. The compound of claim 9 wherein $X^1$=$NR^7$;

$R^2$, $R^3$, $R^4$, $R^5$ and $R^6$ are each hydrogen; and $R^7$ is $C_{1-4}$alkyl that is optionally substituted with phenyl.

12. The compound of claim 9 wherein $X^1$=$NR^7$; $R^2$, $R^3$, $R^4$, $R^5$, and $R^6$ are each hydrogen; and $R^7$ is $C_{3-4}$ alkenyl that is optionally substituted with 1 substituent selected from the group consisting of alkyl and aryl wherein the alkenyl point of attachment is not at an unsaturated carbon.

13. The compound of claim 9 wherein =$NR^7$;

$R^2$, $R^3$, $R^4$, $R^5$, and $R^6$ are each hydrogen; and $R^7$ is $C_3$ alkenyl wherein the alkenyl point of attachment is not at an unsaturated carbon.

14. The compound of claim 9 wherein $X^1$=$NR^7$;

$R^2$, $R^3$, $R^4$, $R^5$, and $R^6$ are each hydrogen; and $R^7$ is $C_{3-4}$ alkynyl that is optionally substituted with 1 substituent selected from the group consisting of alkyl and aryl wherein the alkynyl point of attachment is not at an unsaturated carbon.

15. The compound of claim 9 wherein $X^1$=$NR^7$;

$R^2$, $R^3$, $R^4$, $R^5$, and $R^6$ are each hydrogen; and $R^7$ is $C_3$ alkynyl wherein the alkynyl point of attachment is not at an unsaturated carbon.

16. The compound of claim 8 wherein R' and R" are individually selected from the group consisting of hydrogen, lower alkyl, and substituted lower alkyl.

17. A compound having the formula:

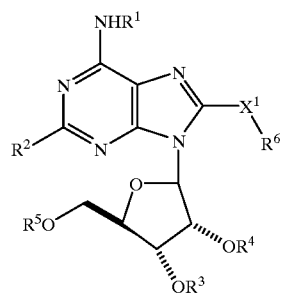

wherein X¹=O, or NR⁷;
R¹ is selected from the group consisting of 3-tetrahydrofuranyl, 3-tetrahydrothiofuranyl, 4-pyranyl, and 4 thiopyranyl.
R², R³, R⁴, R⁵ and R⁶ are each hydrogen; and
R⁷ is $C_{1-6}$ alkyl wherein the alkyl is optionally substituted with 1 substituent selected from the group consisting of alkyl or aryl wherein the optional aryl substituent is further optionally substituted with a substituent selected from the group consisting of halo, alkyl, and $CF_3$.

18. The compound of any one of claims 1–6 or 11–15 wherein R¹ is selected from the group consisting of 3-tetrahydrofuranyl, 3-tetrahydrothiofuranyl, 4-pyranyl, and 4 thiopyranyl.

19. The compound of any one of claims 1–6 or 11–15 or 17 wherein R¹ is 3-tetrahydrofuranyl.

20. A method for modifying cardiac activity in a mammal experiencing a heart electrical disorder comprising administering a therapeutically effective amount of a compound of claim 1 to the mammal.

21. The method of claim 20 wherein the therapeutically effective amount ranges from about 0.01 to about 100 mg/kg weight of the mammal.

22. A pharmaceutical composition comprising the compound of claim 1 and one or more pharmaceutical excipients.

23. The pharmaceutical composition of claim 22 in the form of a solution.

24. The pharmaceutical composition of claim 22 in the form of a tablet.

* * * * *